United States Patent [19]

Lutz

[11] Patent Number: 5,520,757

[45] Date of Patent: May 28, 1996

[54] LOW VULNERABILITY PROPELLANTS

[75] Inventor: Rocco G. Lutz, Tresckow, Pa.

[73] Assignee: ICI Explosives USA Inc., Tamaqua, Pa.

[21] Appl. No.: 236,601

[22] Filed: Aug. 25, 1988

[51] Int. Cl.[6] .................................................. C06B 25/34
[52] U.S. Cl. .......................................... 149/92; 149/109.6
[58] Field of Search ..................................... 149/109.6, 92

[56] References Cited

U.S. PATENT DOCUMENTS

| | | | |
|---|---|---|---|
| H448 | 3/1988 | Farncomb et al. ....................... | 149/104 |
| 2,461,582 | 12/1944 | Wright et al. . | |
| 2,485,855 | 12/1944 | Blomquist et al. . | |
| 2,678,946 | 12/1944 | Blomquist et al. . | |
| 3,423,256 | 1/1969 | Griffith ........................................ | 149/2 |
| 4,352,699 | 10/1982 | Zeigler, Jr. ............................ | 149/109.6 |
| 4,381,958 | 5/1983 | Howard . | |
| 4,450,110 | 5/1984 | Simmons et al. . | |
| 4,457,791 | 7/1984 | Gill et al. ................................ | 149/19.3 |
| 4,522,756 | 1/1985 | Schack et al. ........................... | 260/349 |
| 4,567,296 | 1/1986 | Adams, Jr. et al. ..................... | 564/111 |
| 4,726,919 | 2/1988 | Kristofferson et al. .................. | 264/33 |
| 4,761,250 | 8/1988 | Frankel et al. ........................... | 260/349 |

FOREIGN PATENT DOCUMENTS 95939  4/1978  Poland .

*Primary Examiner*—Donald P. Walsh
*Assistant Examiner*—Anthony R. Chi
*Attorney, Agent, or Firm*—Charles Q. Buckwalter

[57] ABSTRACT

This invention record describes the production of a low vulnerability propellant (LOVA) ingredients utilizing mixtures of alkyl nitratoethyl nitramines (alkyl NENAs) and/or bis(2-nitroxyethyl)nitramine (DINA) with nitrocellulose. Described compositions provide lower freezing points and decreases sensitivity while maintaining or surpassing output realized with currently used nitroglycerins/nitrocellulose mixtures. A process to provide for the production of desired mixtures of alkyl NENAs with each other or with DINA in a safe, cost-effective co-nitration process is disclosed. The process involves mixing together predetermined amounts of precursors for each of alkyl NENAs and/or DINA to be present in the final mix. Nitrating the precursors followed by a catalyst reaction, wash and neutralization step.

20 Claims, 3 Drawing Sheets

LOW VULNERABILITY PROPELLANTS

FIELD OF THE INVENTION

The present invention relates to propellant ingredients and, utilizing mixtures of nitro ester/nitramines in propellant formulations. The invention also relates to a method of preparing the nitro esters/nitramines (NENA) by co-nitration.

BACKGROUND OF THE INVENTION

Energetic materials such as the nitro ester/nitramines described in this invention record are utilized in the production of gun and rocket propellants. Propellants differ from explosives primarily in regard to their burning rates. Many propellants utilize explosives such as nitroglycerine or a mixture of explosives with various modification agents. There has been a need for a replacement for nitroglycerin in making gun propellants. It has been desired to achieve a nitroglycerin replacement with lower vulnerability, primarily to initiation. It has been desired to produce a low vulnerability (LOVA) propellant which is significantly less sensitive to initiation than standard nitro ester propellants while maintaining a low freezing point.

The freezing point of a compound used in formulation of a propellant is of importance. A lower freezing point is desirable because it prevents or minimizes crystallization of the propellant mixture when subjected to cold weather. However, few compounds with low freezing points possess desired explosive properties. Thus, there has been a need to provide a material that will easily form colloidal mixtures with nitrocellulose, have a low freezing point, is less sensitive to handle than nitroglycerin, but yet has comparable energy qualities or impetus to nitroglycerin.

NENA (nitrate ethyl nitramines) compounds have been explored as possible nitroglycerin replacements. They are hybrid molecules which contain a nitro ester group (as in nitroglycerin) and a nitramine group (as in HMX or RDX). These compounds are less sensitive to impact and friction than nitroglycerin and some have a lower freezing point than nitroglycerin. However, typically colloidal mixtures of the NENA compounds with nitrocellulose exhibit a lower impetus than those of nitroglycerin with nitrocellulose. Various NENA compounds and processes for producing them are disclosed in U.S. Pat. Nos. 2,485,855 and 2,678,946. U.S. Pat. No. 2,461,582 discloses a series of nitroxyalkyl nitramines and a method for their preparation and purification. In particular this patent discloses dinitroxydiethyl nitramine commonly called DINA. The patent reveals the use of DINA in nitrocellulose colloids.

U.S. Pat. No. 4,381,958 discloses propellant compositions containing triaminoguanidene nitrate (TAGN) as an oxidizer and a liquid energetic plasticizer-binder to improve thermal stability when used with resorcinol. The patent also discloses use of NENA as a plasticizer component.

U.S. Pat. No. 4,450,110 discloses azido nitramine 1,5-diazido-3-nitrazapentane (DIANP) and its use in gun and rocket propellants. The DIANP was prepared by first preparing a solution of DINA.

The present invention relates to a composition formed by admixture of compounds to provide low freezing point and yet provide good impetus in the formulation of propellants from the mixtures.

SUMMARY OF THE INVENTION

The present invention provides a composition and method of manufacturing mixtures of two or more of the compounds alkyl-NENA and DINA. In one aspect, the invention relates to the mixtures of these compounds. In the preferred embodiment, a composition for use in propellants is a mixture of two or more of the following compounds DINA, Methyl-NENA, Ethyl-NENA, Propyl-NENA, Butyl-NENA. In another aspect, the invention relates to the formation of colloids of these mixtures with nitrocellulose to provide improved propellants. The present invention also provides a method for co-nitration of DINA with one or more of the NENA compounds. A mixture of alkyl alcohol amines and dialcohol amines are precursors of the final product are combined in a suitable ratio to obtain the desired final product at the completion of co-nitration. The mixture of precursors is slowly added to an excess of concentrated nitric acid with agitation and cooling to maintain the temperature between from about 40° to about 60° F. After completion of the reaction of the precursors and the nitric acid, a dehydrating agent is added to the solution and a halogen catalyst is added at the mixture is heated to a temperature in the range from about 70° to about 120° F. The temperature of the mixture is maintained in that range and the mixture is agitated until completion of the second reaction. Thereafter, the product mixture is neutralized with a dilute base. The product can then be separated.

In another aspect, the invention provides for co-nitration of two or more of the NENA compounds, by a similar co-nitration process.

DETAILED DESCRIPTION

The present invention relates to utilization of a composition formed by admixture of two or more compounds from the group of alkyl nitrate ethyl nitramines and dinitroxy diethyl nitramine. The invention also relates to the utilization of these compositions or a mixture of these compositions in a colloidal mixture with nitrocellulose to produce propellants and rocket fuels.

The compounds useful in making the compositions of the present invention include alkyl nitrate ethyl nitramines and in particular the homologous series based on N-(2-nitroxyethyl) nitramine, $NO_2$—N—$CH_2CH_2ONO_2$, (herein "NENA"). The compounds include N-(2-nitroxyethyl) methylnitramine (herein "Methyl NENA"); N-(2-nitroxyethyl) ethylnitramine (herein "Ethyl-NENA"); N-(2-nitroxyethyl) n-propylnitramine (herein "Propyl-NENA"); N-(2-nitroxyethyl) n-butylnitramine (herein "Butyl-NENA"); N-(2-nitroxypropyl) methylnitramine and N-(2-nitroxyethyl) cyclohexylnitramine (herein "cyclohexyl-NENA"). The compounds also include bis (2-nitroxyethyl) nitramine (herein "DINA").

The alkyl-NENA's of primary interest are ethyl-NENA, methyl-NENA, propyl-NENA and butyl-NENA. The preferred compositions of the present invention are made utilizing two or more of the following compounds: Butyl- NENA, ethyl-NENA, methyl-NENA, and DINA. DINA is a crystalline material at room temperature and melts at 50°–52° C. Butyl-NENA is liquid at room temperature and freezes at −9° C. Methyl-NENA is a crystalline solid at room temperature and melts at 38°–40° C. Ethyl-NENA is a liquid at room temperature and freezes at 2°–4° C. Nitroglycerin is a viscous liquid at room temperature and freezes at 13.1° C. Thus, the freezing points of methyl-NENA and DINA are substantially higher than the freezing point of nitroglycerin. The freezing points of ethyl-NENA and butyl-NENA are less than that of nitroglycerin.

Figure 2:
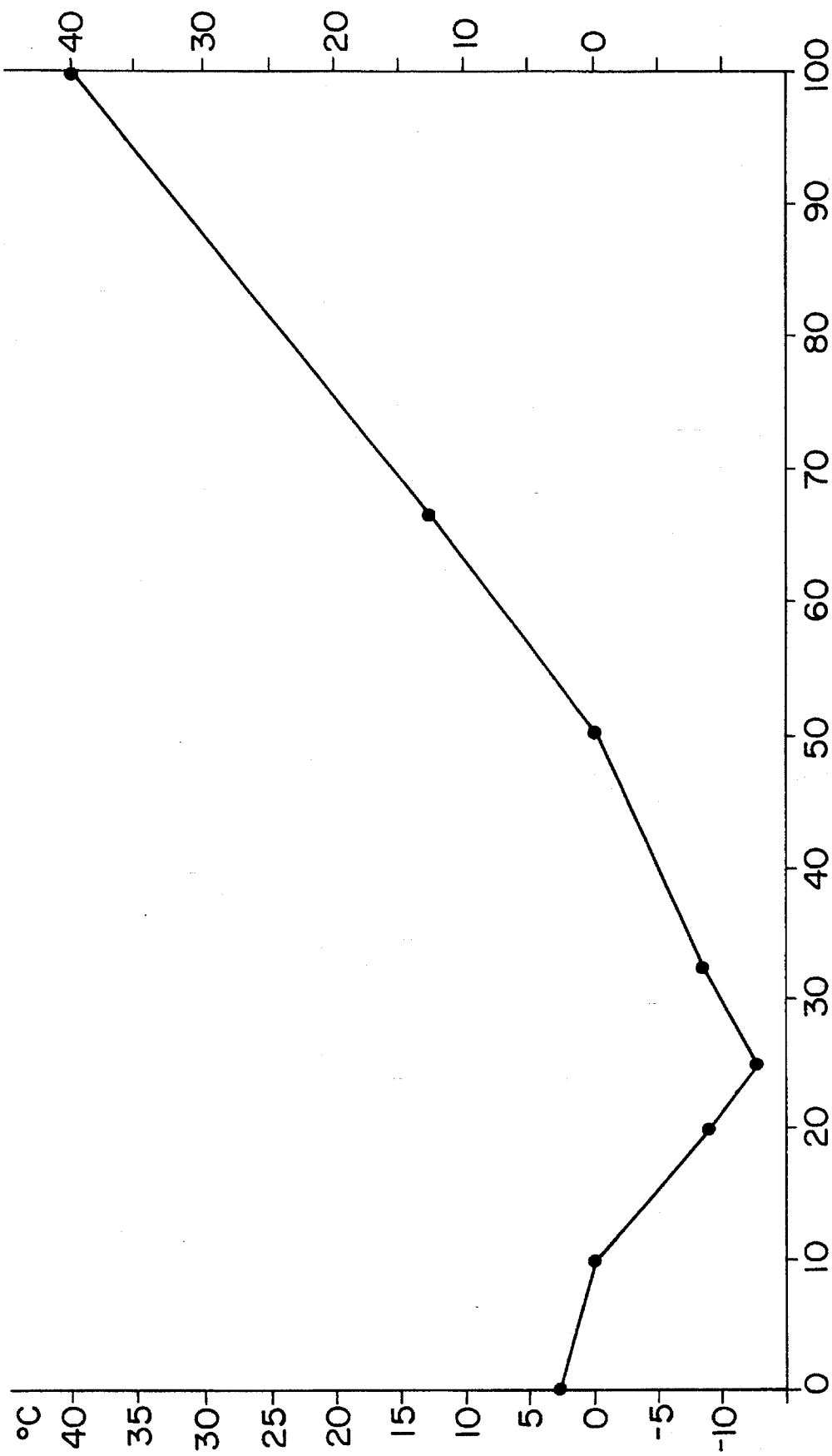
FIG. 2 illustrates the eutectic point achieved by mixtures of methyl NENA and ethyl NENA.
Figure 3:
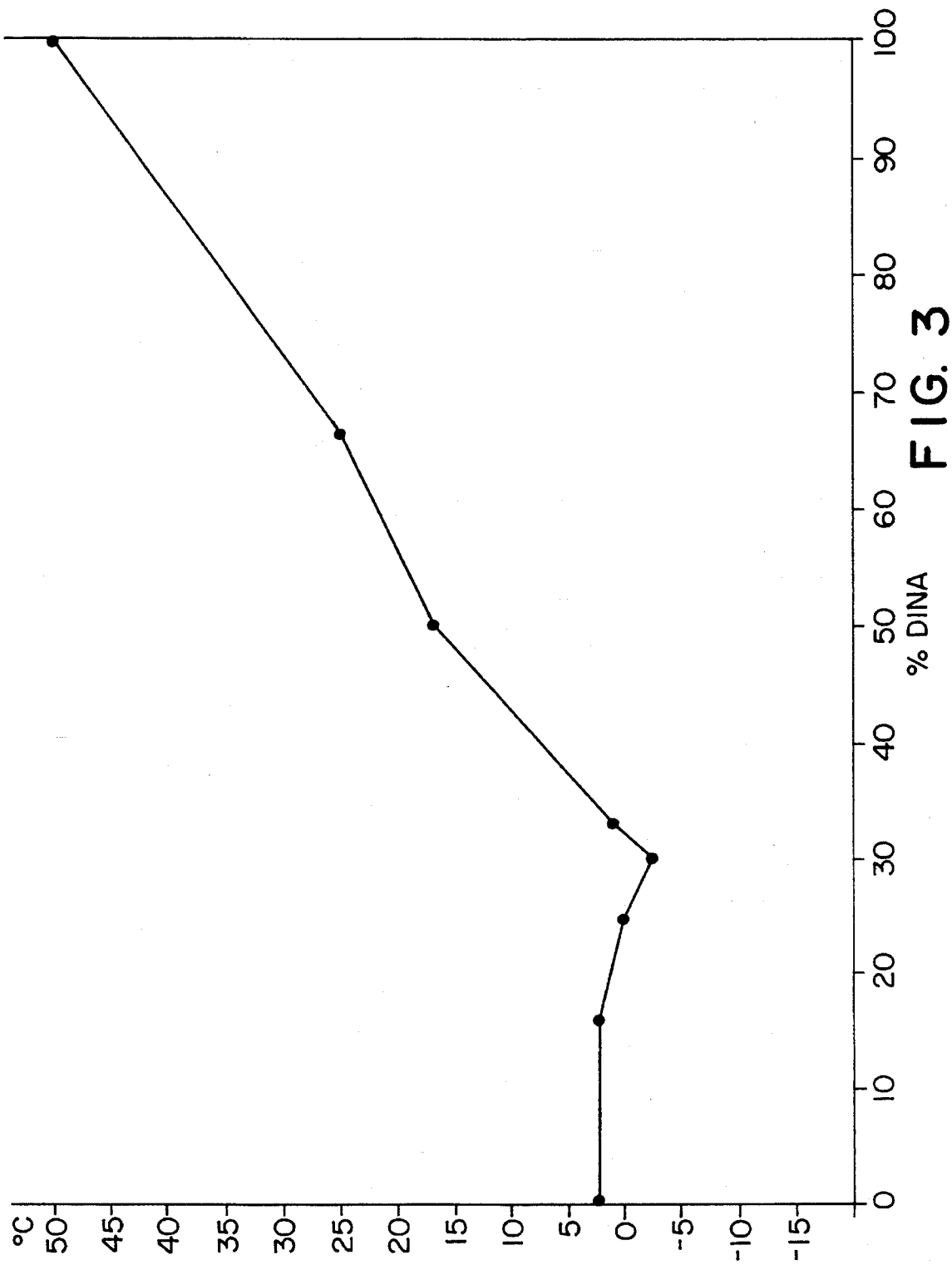
FIG. 3 is a eutectic curve for mixtures of ethyl-NENA and DINA.

It has been discovered that a mixture of two or more of the compounds from the group consisting of alkyl-NENA's and DINA produce surprising results and can form colloidal mixtures with nitrocellulose to produce propellant compositions with impetus similar to that of propellant compositions made with nitroglycerin while being safer to manufacture than propellants utilizing nitroglycerin. While Methyl NENA and DINA have excellent impetus they have high melting points which are disadvantageous for many propellant applications. Ethyl-NENA has a low melting point but provides only fair impetus in colloidal mixtures With nitrocellulose. The larger NENA's, propyl-NENA, butyl-NENA have poor impetus but are much lower in freezing point. It has been discovered that mixture of two or more alkyl-NENA's produce eutectic mixtures with lower freezing points than the separate components. Similarly mixtures of one or more alkyl NENA with DINA produce eutectic mixtures. It has been discovered that mixtures of these compounds result in surprisingly useful compositions. FIGS. 2 and 3 are eutectic diagrams. FIG. 2 is a eutectic diagram showing admixtures of methyl-NENA and ethyl-NENA. As can been seen from FIG. 2, the lowest freezing point is obtained with a mixture containing approximately 25% methyl-NENA and 75% ethyl-NENA, which has a freezing point of approximately −12° C. FIG. 3 demonstrates admixtures of ethyl-NENA and DINA demonstrating that the lowest freezing point is for a mixture of approximately 30% DINA with 70% ethyl-NENA. (all percentages herein are weight percentages unless otherwise specified.) The freezing point of that mixture is approximately −2.5° C. Thus, by utilizing mixtures of ethyl-NENA with either methyl-NENA or DINA one can formulate a mixture which optimizes freezing point considerations with energy and sensitivity considerations to tailor propellants to various use environments. Of course mixtures of the other alkyl-NENA compounds can be made as well as mixtures of DINA with alkyl-NENA's. In the preferred embodiments, the mixtures will include either methyl-NENA, DINA or a combination of the two, because of the good impetus properties they impart to an admixture. The compositions of the present invention will generally comprise 10% to 90% of a compound selected from the groups comprising NENA, DINA and mixtures thereof with other alkyl-NENA's. The composition of the present invention can also be a mixture of from 10–90% methyl-NENA with 10–90% DINA by weight. A preferred embodiment is a mixture of from 25% to 90% methyl-NENA with 10 to 75% ethyl-NENA. Another preferred embodiment is a mixture of from 10 to 80% DINA with 20 to 90% ethyl-NENA For low temperature applications particularly useful compositions are made from 10% to 55% methyl-NENA together with 45 to 90% ethyl-NENA or from 15% to 40% DINA with 60 to 85% ethyl-NENA.

The mixtures of the present invention are useful in preparation of propellant compositions. Generally they are used in colloidal mixtures with from about 10 to 90 percent of nitrocellulose.

EXAMPLE 1

A mixture of methyl and ethyl-NENA was prepared in the amount of 50% by weight methyl-NENA and 50% by weight ethyl-NENA. The composition had a freezing point of approximately 0° C. The impetus of this mixture was equal to that of a colloidal mixture of nitroglycerin with 36% nitrocellulose. The mixture of methyl-NENA and ethyl-NENA had a desirably low freezing point, easily formed a colloidal mixture with nitrocellulose and was less sensitive than nitroglycerin.

EXAMPLE 2

A mixture which is highly desirable for low temperature applications was made by mixing 25% by weight methyl-NENA with 75% by weight ethyl-NENA. This mixture gave an impetus equal to that of nitroglycerin when mixed with 20% nitrocellulose.

EXAMPLE 3

A mixture was formed from 33% DINA with 66% ethyl-NENA. The resulting mixture had a freezing point of 1° C. A colloidal mixture with nitrocellulose resulted in a higher impetus than most compositions of nitroglycerin mixed with nitrocellulose.

Thus, the present invention provides for a wide range of mixtures of DINA and ethyl-NENA which have freezing points lower than nitroglycerin as shown by FIG. 3. These mixtures have a higher energy capacity than nitroglycerin while offering the advantage of being less sensitive than nitroglycerin. Similarly, many admixtures of methyl-NENA and ethyl-NENA may be produced which have lower freezing points than nitroglycerin while being less sensitive than nitroglycerin and still exhibiting comparable energy capacity.

Figure 1:
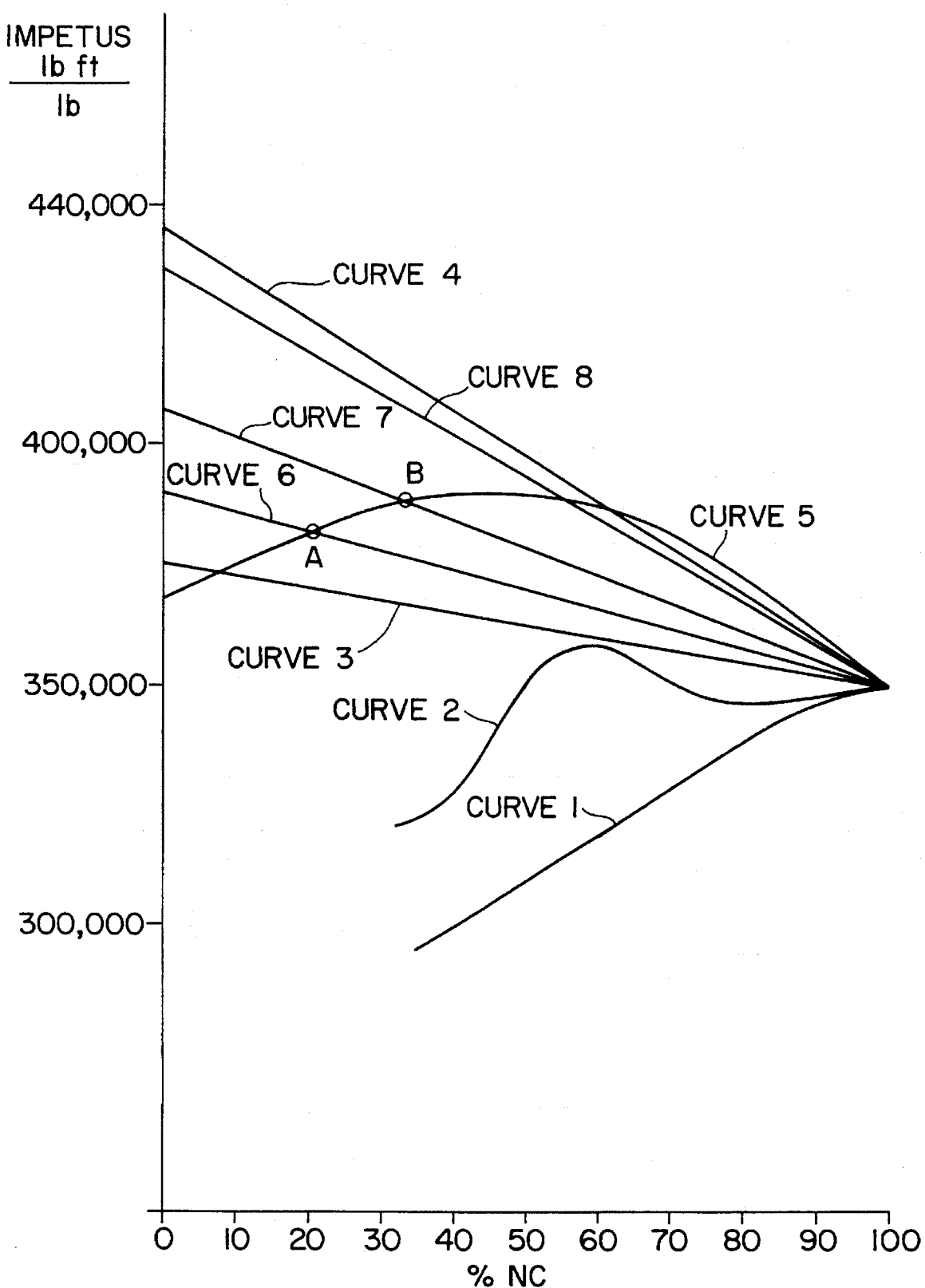
FIG. 1 is a draft relating theoretical impetus with percent of nitrocellulose in colloids with various NENA compounds.

FIG. 1 sets forth a graph comparing the theoretical impetus of various compounds and admixtures in colloidal mixtures with nitrocellulose in comparison to nitroglycerin mixtures with nitrocellulose. The vertical axis of FIG. 1 is the impetus in foot pounds. The horizontal axis of FIG. 1 represents nitrocellulose. The lines in FIG. 1 represent various compounds or compositions which were admixed with nitrocellulose. Curve 1 of FIG. 1 represents butyl-NENA admixed with nitrocellulose, curve 2 represents propyl-NENA when admixed with nitrocellulose, curve 3 represents ethyl-NENA when admixed with nitrocellulose, curve 4 represents methyl-NENA when combined with nitrocellulose, curve 5 represents a mixture of nitroglycerin with nitrocellulose, curve 6 represents the combination of a mixture of 25% methyl-NENA and 75% ethyl-NENA with nitrocellulose, curve 7 represents the combination of an admixture of 50% methyl-NENA and 50% ethyl-NENA with nitrocellulose and curve 8 represents the combination of an admixture of 75% methyl-NENA with 25% ethyl-NENA and nitrocellulose. As can been seen from FIG. 1, point A represents a mixture of approximately 22% nitrocellulose with 78% of a mixture of 25% methyl-NENA and 75% ethyl-NENA produces the impetus equivalent to an admixture of 22% nitrocellulose with 78% nitroglycerin. Point B of FIG. 1 demonstrates that a mixture of 36% nitrocellulose with 64% of a mixture of 50% ethyl-NENA and 50% methyl-NENA produces an impetus equivalent to an admixture of 36% nitrocellulose with nitroglycerin. As demonstrated by FIG. 1, numerous compositions can be made with equivalent impetus of various nitroglycerin and nitrocellulose combinations.

The preferred compositions of the present invention contain 10% to 90% methyl NENA and 10% to 90% of another alkyl NENA's mixture of other alkyl NENA's, DINA or mixtures of DINA with other alkyl NENA's. Another preferred composition of the present invention contains 10% to 90% of an alkyl NENA or mixtures thereof. More preferred compositions are the following compositions:

(A) 10% to 63% methyl-NENA and 47% to 90% ethyl-NENA (B) 10% to 45% DINA and 55% to 90% ethyl-NENA (C) 10% to 55% DINA and 45% to 90% methyl-NENA The compositions of the present inventions can be made by combining the desired proportions of the compounds. This is preferably done by mixing the desired proportions of each compound in the liquid state to achieve a homogeneous mixture. The temperature at which the mixing is performed will depend upon the melting points of the compounds to be mixed. More preferably the compositions of the present invention are formed by the co-nitration process of the present invention.

In another aspect, the present invention relates to a method for the co-nitration of alkyl-NENA's. Another aspect relates to the co-nitration of DINA and one or more alkyl-NENA's. The process involves the co-nitration of admixtures of two or more alkyl alcohol amines to produce a final mixture of two or more NENA-compounds or the mixture of a dialcohol amine with one or more alkyl alcohol amines to produce a final mixture of DINA with one or more NENA compounds. It has been discovered that co-nitration of mixtures to achieve the compositions of the present invention is a safe, effective, and time saving method of production. Such co-nitration is highly desirable because it allows production of the desired mixture of alkyl-NENA's or alkyl-NENA's and DINA. The process is highly desirable because it minimizes handling of explosive compositions, reduces the process and time for production, increases safety by eliminating recrystallization and mixture steps, allows for higher quality by minimizing possible contamination, and facilitates manufacture by allowing utilization of the liquids by avoiding formation of intermediate solids.

In the process of the present invention, a mixture is made of alkyl alcohol amines and dialcohol amines in predetermined amounts. These precursors are admixed in a suitable ratio to obtain the desired final product ratio at the completion of co-nitration. A rough approximation of the amount of starting material for each alkyl alcohol amine can be determined by the separate nitration of each precursor to determine its practical yield, similarly, a rough approximation of the amount of starting dialcohol amines can be determined by separate nitration of each to determine its practical yield. Taking into account these practical yields, the relative portions of various precursors to produce the desired final rates of compounds can be estimated. Thereafter, co-nitration is performed and appropriate adjustments to the relative amounts of the precursor reactants (the dialcohol amine and alkyl alcohol amines) can be made to achieve the desired final composition. Suitable alkyl alcohol amine precursors are methylethanol amine, ethylethanol amine, propylethanol amine and butylethanol amine, as well as other ethanol amines. The dialcohol amine is preferably diethanol amine. Methylethanol amine when nitrated in accordance with the present method will produce methyl-NENA and ethylethanol amine will produce ethyl-NENA. Diethanol amine when nitrated according to the present invention will produce DINA.

The method of the present invention involves first making an admixture of two or more of the compounds of the group alkyl alcohol amines and diethanol amines. The proportions of each compound in a solution is based upon the desired final ratio of alkyl-NENA and DINA in the final composition. The above mixture is slowly added to an excess of concentrated nitric acid with cooling and agitation. The reaction should be maintained at about 30° to about 60° F., (preferably 38° to 42° F.). When the reaction is complete, a dehydrating agent such as acetic anhydride is added to the solution along with a halogen catalyst such as acetylchloride and the temperature is raised to about 70° to 120° F. (preferably 90° to 95° F.). Temperature and agitation are continued until completion of the reaction. Thereafter, the reaction mixture is washed and can be cooled as desired. The mixture can be cooled and washed by adding cold water while agitation is maintained producing a pale yellow viscous liquid. Washing is preferentially performed with warm water at approximately about 90° to about 100° F. Washing for approximately 15 minutes has been found to be sufficient. Thereafter, the product is neutralized with a dilute base such as a dilute solution of sodium carbonate. The resulting lipand product can then be separated from the water and mixed in the desired proportion with nitrocellulose to form a colloidal mixture. The co-nitration process described can be conducted either as a batch process of the reactants involved or as a continuous process.

EXAMPLE 4

A blend of methyl and ethyl-NENA in a ratio of approximately 50% methyl-NENA and 50% ethyl-NENA by weight was prepared by co-nitration. The mixture of 25 grams of methylethanol amine and 25 grams of ethylethanol amine was made. This mixture was then slowly added to 99.2 grams of a 96% nitric acid solution. The temperature of the nitric acid solution was maintained between 43° and 47° F. The addition of the methyl/ethylethanol amine solution to the nitric acid was made over a period of 60 minutes. After completion of addition of the methyl/ethylethanol amine solution to the nitric acid, the reaction mixture was maintained at approximately 45° for 15 minutes with agitation. This resulted in a clear pale-yellow amine/acid mixture. To this amine/acid mixture 146.9 grams of 97% acetic anhydride and 1.3 grams of acetylchloride was slowly added over 19 to 20 minutes. For this addition the temperature of the solutions was kept at between 92° to 95° F. After all of the acetic anhydride and acetylchloride solution had been added, the mixture was maintained at 90° F. with agitation maintained for approximately 15 minutes to allow completion of the reaction. The reaction mixture was then cooled by slowly pouring it into 800 grams of cold water with slow agitation. The resulting solution was a pale-yellow viscous liquid which was collected and then washed with 150 grams of warm water at a temperature of 100° F. for 15 minutes. Thereafter, the solution was neutralized by washing the product with 150 grams of a dilute 6% sodium carbonate solution. The final product yield was 68.1 grams or approximately 65% of the theoretical yield. The composition was analyzed by HPLC and found to be 50.7% methyl-NENA and 49.3% ethyl-NENA. The product had a DSC peak (10° C./min) of 214° C.±2° C. and a freezing point of 0° C.

EXAMPLE 5

A composition of DINA/ethyl-NENA was prepared having 33.3% DINA and 66.7% ethyl-NENA by weight by co-nitration. A mixture of 25.0 grams of diethanol amine with 75.0 grams of ethylethanol amine was prepared. The amine solution thus prepared was slowly added to 179.2 grams of nitric acid (96% solution). The addition of the amine solution to the nitric acid expended 65 minutes and the mixture was maintained at a temperature of between 43° to 47° F. After all of the amine solution had been added to the nitric acid, the resulting mixture was then maintained at 45° F. for 15 minutes with agitation. This produced a clear yellow amine/acid mixture. A solution of 147.9 grams acetic anhydride (97% solution) and 1.10 grams of acetylchloride was prepared. The anhydride/chloride solution was added to one-half of the amine/acid mixture slowly over a period of 20–25 minutes. The temperature of the resulting mixture was maintained in the range of 92° to 95° F. After complete addition of the anhydride/chloride solution to the amine/acid solution, the mixture was agitated for 15 minutes while being maintained at 90° F. to complete the reaction. Thereafter, the reaction mixture was cooled by slowly pouring it into 600 grams of cold water with agitation. This produced a pale-yellow viscous liquid which was washed with 150 grams of warm water at 110° F. for 15 minutes. Thereafter, the product was neutralized by the addition of 150 grams of a dilute sodium carbonate solution (6%) at 100° F. The final product was 81.1 grams of DINA/ethyl-NENA. This represents a yield of 74% of theoretical. Analysis of the product by HPLC demonstrated 33% by weight of DINA and 67% by weight ethyl-NENA. The composition had a DSC-exotherm (10°/min) at 210° C.±2° C. and a freezing point of 1° C.

One skilled in the art will recognize it is possible to make the compositions of this invention from a variety of materials and by a variety of processes. while the preferred embodiments of the present invention have been described in detail, it will be evident that various further modifications are possible without departing from the scope of the invention.

I claim:

1. The method of preparing a mixture of nitro ester/nitramines for propellant formulations, comprising:
   (a) solubilizing predetermined amounts of two or more precursors of alkyl alcohol amines;
   (b) combining the precursor mixture slowly to an excess of concentrated nitric acid while agitating the mixture;
   (c) maintaining the temperature between about 30° to about 60° F. until the reaction of said concentrated nitric acid and precursors is complete;
   (d) adding predetermined amounts of a dehydrating agent and a halogen catalyst to the reaction mixture resulting from step (c);
   (e) heating the solution of step (d) to a temperature in the range of about 70° to about 120° F. and agitating until completion of the mixture formed in step (d);
   (f) washing the reaction mixture with a predetermined amount of warm water; and
   (g) neutralizing the product of step (f) with a dilute base.

2. The method of claim 1 wherein said alkyl alcohol amine precursors are selected from the group consisting of methylethanol amine, ethylethanol amine, propylethanol amine and butylethanol amine.

3. The method of claim 1 wherein the dehydrating agent is acetic anhydride.

4. The method of claim 1 wherein the halogen catalyst is acetyl chloride.

5. The method of claim 1 wherein the dilute base is a dilute solution of sodium carbonate.

6. The method of claim 2 wherein said halogen catalyst is acetyl chloride.

7. The method of claim 1 wherein said precursors are methylethanol amine and ethylethanol amine.

8. The method of claim 7 wherein said halogen catalyst is acetyl chloride.

9. The method of claim 1 further comprising the steps of (h) separating the product of step (g) from the water and (i) colloiding predetermined amounts of the product of step (h) with nitrocellulose.

10. The method of preparing a mixture of nitro ester/nitro amines for propellant formulations comprising:
    (a) solubilizing predetermined amounts of one or more precursors of alkyl alcohol amines together with a dialcohol amine;
    (b) combining the precursor mixture slowly to an excess of concentrated nitric acid while agitating the mixture;
    (c) maintaining the temperature between about 30° to about 60° F. until the reaction of said concentrated nitric acid and precursors is complete;
    (d) adding predetermined amounts of a dehydrating agent and a halogen catalyst to the reaction mixture resulting from step (c);
    (e) heating the solution of step (d) to a temperature in the range of about 70° to about 120° F. and agitating until completion of the reaction of the mixture formed in step (d);
    (f) washing the reaction mixture with a predetermined amount of warm water; and
    (g) neutralizing the product of step (f) with a dilute base.

11. The method of claim 10 wherein said alkyl alcohol amine precursors are selected from the group consisting of methylethanol amine, ethylethanol amine, propylethanol amine and butylethanol amine.

12. The method of claim 10 wherein the dialcohol amine precursor is diethanol amine.

13. The method of claim 11 wherein said dialcohol amine precursor is diethanol amine.

14. The method of claim 10 wherein the dehydrating agent is acetic anhydride.

15. The method of claim 10 wherein the halogen catalyst is acetyl chloride.

16. The method of claim 13 wherein said catalyst is acetylchloride.

17. The method of claim 10 wherein said alkyl alcohol amine precursor is ethylethanol amine and said dialcohol amine precursor is diethanol amine.

18. The method of claim 17 wherein said halogen catalyst is acetylchloride.

19. The method of claim 18 wherein said dilute base is a dilute solution of sodium carbonate.

20. The method of claim 10 further comprising steps of (h) separating the product of step (g) from the water and (i) colloiding predetermined amounts of the product of step (h) with nitrocellulose.

* * * * *